US00PP27748P3

(12) United States Plant Patent
Suzuki

(10) Patent No.: US PP27,748 P3
(45) Date of Patent: Mar. 7, 2017

(54) ***LOROPETALUM* PLANT NAMED 'KURENAI DAIOU'**

(50) Latin Name: *Loropetalum chinense*
Varietal Denomination: KURENAI DAIOU

(71) Applicant: Yuji Suzuki, Kawaguchi (JP)

(72) Inventor: Yuji Suzuki, Kawaguchi (JP)

(73) Assignee: Spring Meadow Nursery Inc., Grand Haven, MI (US)

( * ) Notice: Subject to any disclaimer, the term of this patent is extended or adjusted under 35 U.S.C. 154(b) by 83 days.

(21) Appl. No.: 14/544,870

(22) Filed: Feb. 26, 2015

(65) Prior Publication Data

US 2016/0262294 P1 Sep. 8, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Loropetalum* cultivar named 'KURENAI DAIOU' is disclosed, characterized by extremely large burgundy colored foliage. Additionally it has an upright very dense growing form, and larger than average petals. The new variety is a *Loropetalum*, normally produced as an outdoor garden or container plant.

2 Drawing Sheets

Figure 1:
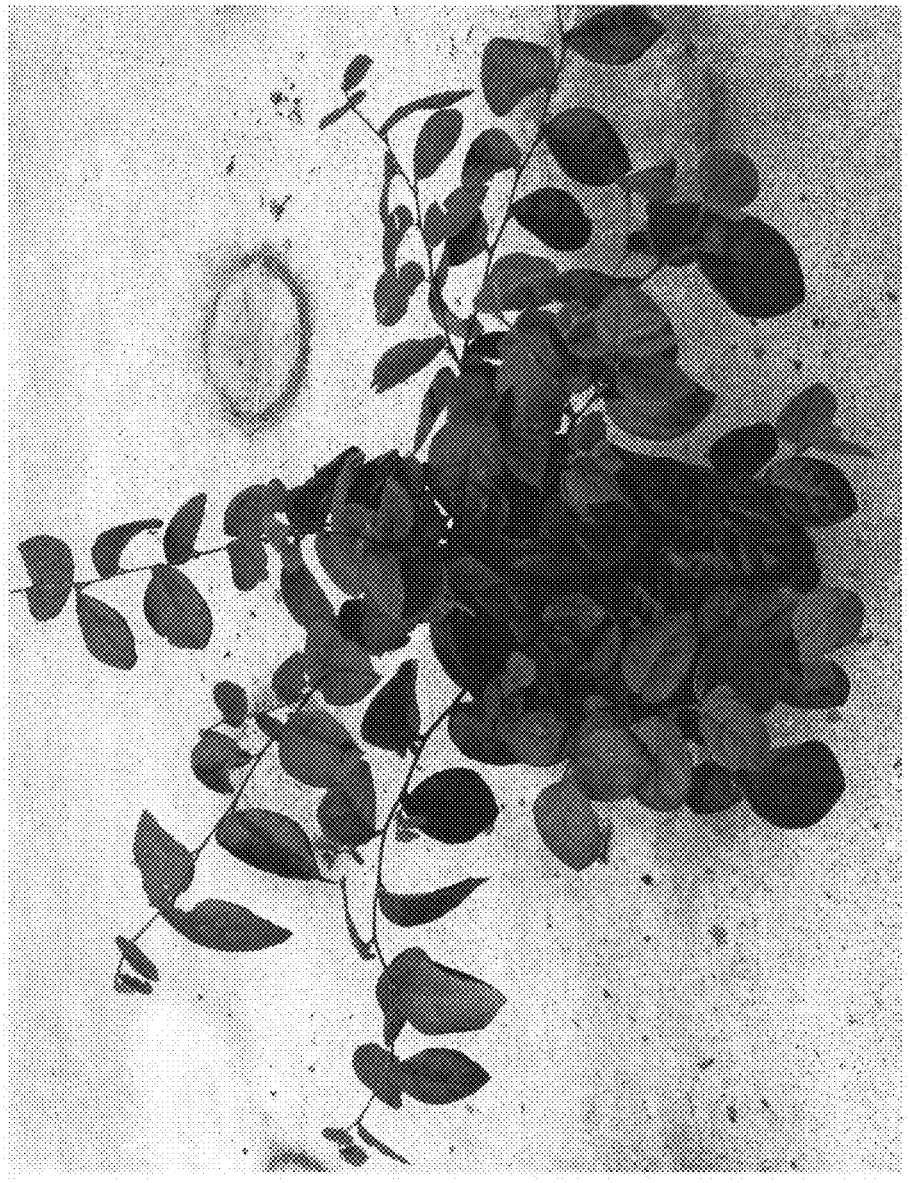

Latin name of the genus and species: *Loropetalum chinense*.

Variety denomination: 'KURENAI DAIOU'.

BACKGROUND OF THE INVENTION

The new *Loropetalum* cultivar is a product of a planned breeding program conducted by the inventor, Yuji Suzuki, in Kawaguchi City, Saitama, Japan. The objective of the breeding program was to produce new *Loropetalum* varieties with better foliage color and improved flowering for ornamental commercial applications. The cross resulting in this new variety was made during Apr. 20, 2005.

The seed parent is the, unpatented, propriety variety referred to as *Loropetalum* '1-8'. The pollen parent is the unpatented, propriety variety referred to as *Loropetalum* '1-30'. The new variety was discovered in a commercial nursery by the inventor in a group of seedlings resulting from the 2005 crossing, in Kawaguchi City, Saitama, Japan.

Asexual reproduction of the new cultivar was performed by softwood cuttings. This was first performed at a commercial nursery in Kawaguchi City, Saitama, Japan, in 2010 and has shown that the unique features of this cultivar are stable and reproduced true to type in 5 successive generations.

SUMMARY OF THE INVENTION

The cultivar 'KURENAI DAIOU' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KURENAI DAIOU' These characteristics in combination distinguish 'KURENAI DAIOU' as a new and distinct *Loropetalum* cultivar:

1. Extremely large, attractive foliage compare to other *Loropetalum* (6.0 cm long 4.4 cm wide).
2. Consistent and uniform upright growth habit (5-6')
3. Very dense and full growing plant.
4. Eye-catching, larger than average petals (2.4 cm).
5. Nice burgundy foliage color.

Plants of the new cultivar 'KURENAI DAIOU' are similar to plants of the seed parent, *Loropetalum* '1-8' in most horticultural characteristics, however, plants of the new cultivar 'KURENAI DAIOU' differ in the following;

1. Magenta/pink flowers. The seed parent flower color is dark red.
2. Very large, elliptical leaves. The parent's leaves smaller and ovate.
3. Upright growth habit. The parent growth habit is spreading.
4. Dark red foliage. The parent's foliage is nearly black.

Plants of the new cultivar 'KURENAI DAIOU' are similar to plants of the pollen parent, *Loropetalum* '1-30' in most horticultural characteristics, however, plants of the new cultivar 'KURENAI DAIOU' differs in the following;

1. Magenta/pink flowers. The parent flower color is dark red.
2. New variety foliage is much larger than pollen parent foliage.
3. Blackish-red foliage. The parent's foliage is nearly black.

COMMERCIAL COMPARISON

Plants of the new cultivar 'KURENAI DAIOU' are comparable to the patented, commercial variety *Loropetalum* 'Shang-hi' U.S. Plant Pat. No. 18,331. The two *Loropetalum* varieties are similar in most horticultural characteristics; however, the new variety 'KURENAI DAIOU' differs in the following:

1. Larger foliage, ranging from 2.5-6.0 cm long and 2.0-4.4 cm wide compared to 4.2 cm long and 2.3 cm wide for those of the comparator.
2. Longer petals, 2.4 cm compared to 1.7 cm of the comparator.
3. Taller habit, 5-6' compared to 4-5' for the comparator.

BRIEF DESCRIPTION OF THE PHOTOGRAPHS

The accompanying photograph in FIG. 1 illustrates in full color a typical plant of 'KURENAI DAIOU' grown in a 1 gallon pot. Age of the plant photographed is approximately 1 to 2 years old from a rooted cutting.

Figure 2:
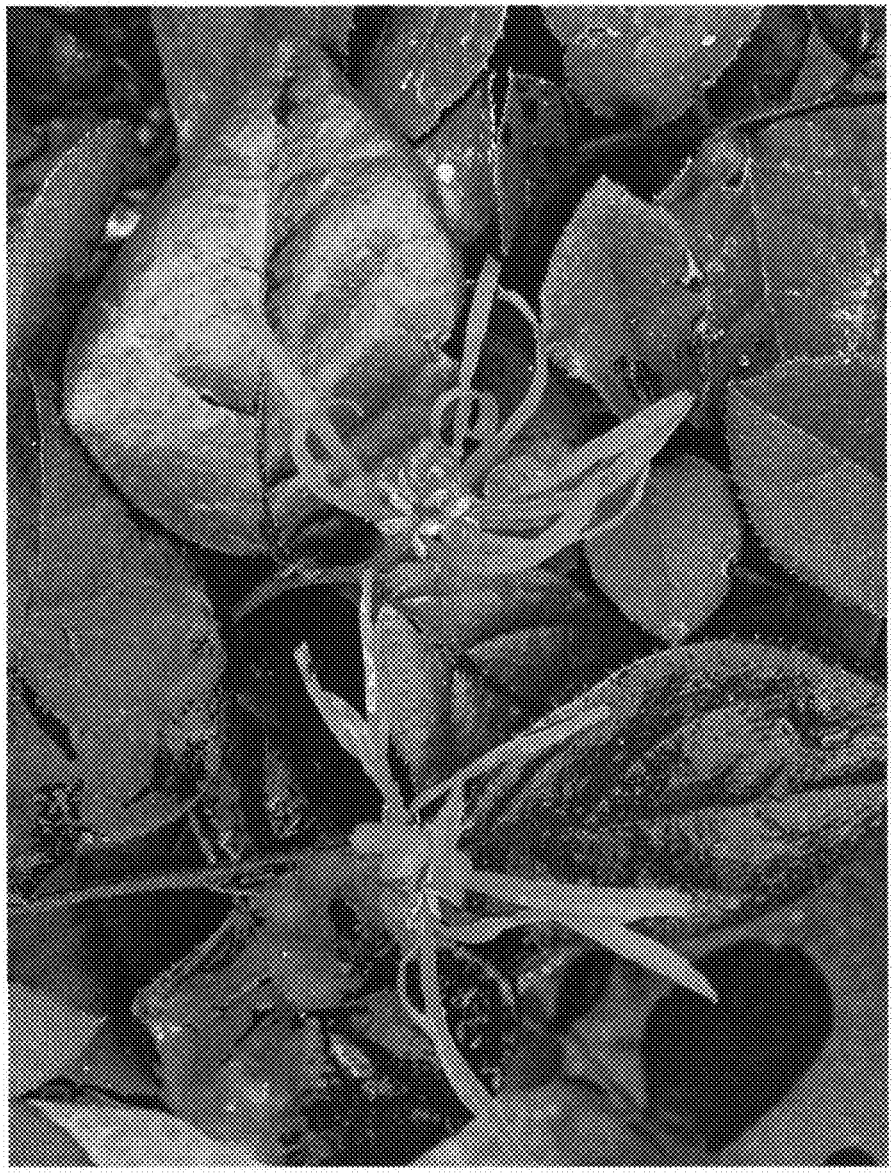

FIG. 2 illustrates a close up of the foliage and flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'KURENAI DAIOU' plants grown in a greenhouse, in Grand Haven Mich. The growing temperature averaged from 60-65° F. during the day and from 40-50° F. during the night. Growing conditions are double poly from Fall through Winter heated to 35° F. The poly was removed in the Spring. Shade cloth was used through the Summer. Measurements and numerical values represent averages of typical plant types.

Botanical classification: *Loropetalum* 'KURENAI DAIOU'.

PROPAGATION

Type of propagation typically used: Cutting.
Time to initiate roots: 18 days at 27° C.
Number of days to produce a rooted liner in summer: 110 days at 27° C.
Root description: Medium to thick, fibrous, free branching and fleshy. Roots are purple to brown in color.

PLANT

Type of plant: Perennial shrub.
Age of plant described: Approximately 2 years old.
Container size of the plant described: 1 gallon.
Appropriate containers sizes: 1 gallon and 2 gallon.
Growth habit: Rounded, upright.
Height: 60-72 inches.
Plant spread: 60-72 inches.
Growth rate: Moderate to rapid.
Plant vigor: Good.
Branching characteristics: Lateral and some basal branching.
Pinching required: Yes, increases branching.
Characteristics of primary lateral branches:
- *Length.*—25 cm.
- *Quantity.*—9.
- *Diameter.*—3 mm. Color: Young stems: Near RHS Greyed-orange 165A. Older stems: Near RHS Brown 200C.
- *Aspect.*—20-50°.
- *Strength.*—Good.

Internode length: 1.8 cm.

FOLIAGE

Leaf:
- *Arrangement.*—Alternate, Single.
- *Quantity.*—Approximately 30 per branch.
- *Average length.*—2.5-6.0 cm.
- *Average width.*—2.0-4.4 cm.
- *Shape of blade.*—Elliptical to broad elliptic.
- *Tip.*—Acute.
- *Base.*—Oblique.
- *Margin.*—Entire.
- *Texture of top surface.*—Slightly rough due to pubescence.
- *Texture of bottom surface.*—Ribbed due to protruding veins. Strong pubescence on veins and midribs.
- *Color.*—Young foliage upper side: Near RHS Greyed-purple 187A. Young foliage under side: Glaucous. Near RHS Red-purple 59A. Mature foliage upper side: Near RHS Black 202A with undertones of green. Mature foliage under side: Glaucous. Near RHS Greyed-green 191B.
- *Venation.*—Type: Pinnate. Venation color upper side: Midribs and veins are depressed on the upper side. Color same as the leaf color. Venation color under side: Midribs and veins are prominent on the underside. Near RHS Greyed-purple Group 186A.
- *Petiole.*—Length: 0.3 to 0.5 cm. Diameter: 1.5 mm. Color: Near RHS Brown 200C.
- *Durability of foliage to stresses.*—Good.

FLOWER

Inflorescence and flower type and habit: Perfect flowers, comprised of strap-shaped petals, occurring in terminal (mainly) and axillary (occasionally) umbels.
Quantity of flowers per inflorescence: 5-7.
Flower type: Perfect, strap-shape, self-cleaning.
Flower aspect: Upright and outward.
Quantity of flowers per lateral stem: 15-30.
Quantity of flowers per plant: 50-500 depending on maturity.
Natural flowering season: Spring to Fall. Begins blooming in Spring, new Blooms (reblooming) occurs until Fall.
Fragrance: None.

Bud:
- *Shape.*—Obovate.
- *Length.*—5 mm.
- *Diameter.*—4 mm.
- *Color.*—Near RHS Red-purple 60C.

Petals:
- *Quantity per flower.*—4.
- *Shape.*—Linear.
- *Margin.*—Entire.
- *Texture.*—Smooth, silky.
- *Appearance.*—Ribbon-like.
- *Length.*—2.4 cm.
- *Width.*—0.2 cm.
- *Tip.*—Truncate.
- *Color.*—When opening: Upper surface: Near RHS Red-purple 61B. Lower surface: Near RHS Red-purple 61B. Fully opened: Upper surface: Near RHS Red-purple 61B. Lower surface: Near RHS Red-purple 61B. Petal color fading to: Near RHS Red-purple 61A.

Sepals:
- *Quantity per flower.*—4.
- *Appearance.*—Slightly pubescent.
- *Arrangement.*—Whorl.

*Shape*.—Ovate and fused, slightly curled outward.
*Length*.—4 mm.
*Width*.—3 mm.
*Tip*.—Slightly reflexed.
*Base*.—Fused.
*Margin*.—Entire, smooth.
*Color*.—Immature upper and lower side: Near RHS Red-purple 60B. Mature upper and lower side: Near RHS Red-purple 59D.

REPRODUCTIVE ORGANS

Stamens:
*Number*.—4.
Pistil:
*Number*.—2.

OTHER CHARACTERISTICS

Lowest temperature tolerant to: 5 to 10° F.
Disease/pest resistance: No unusual susceptibility to diseases or pests noted to date.
Fruits and seeds: Rarely observed. If produced, capsule size is approximately 9 mm long by 7 mm wide. Mature capsule colored between Greyed-Brown 199B and Greyed-Orange 174B. Very few seeds observed within capsule.
Drought tolerance: Moderate to good drought tolerance once established.

What is claimed is:

1. A new and distinct cultivar of *Loropetalum* plant named 'KURENAI DAIOU' as herein illustrated and described.

* * * * *